United States Patent [19]
Johson

[11] Patent Number: 5,199,375
[45] Date of Patent: Apr. 6, 1993

[54] FOLDING WARNING MARKER

[76] Inventor: Mike V. Johson, 1602 SW. 2nd St., Bentonville, Ark. 72712

[21] Appl. No.: 775,501

[22] Filed: Oct. 15, 1991

[51] Int. Cl.⁵ .............................................. E01F 9/01
[52] U.S. Cl. ..................................... 116/209; 40/610; 40/612; 116/63 P; 116/63 T
[58] Field of Search ......................... 116/209, 63, 63 P; 40/603, 610, 612

[56] References Cited

U.S. PATENT DOCUMENTS

| | | | |
|---|---|---|---|
| 2,887,983 | 5/1959 | Budd | 116/63 T |
| 3,200,786 | 8/1965 | Swezy et al. | 116/63 P |
| 3,291,096 | 12/1966 | Walter | |
| 3,777,428 | 12/1973 | Caufield | 116/63 P X |
| 4,055,840 | 10/1977 | Uchytil et al. | |
| 4,209,928 | 7/1980 | Kraayvanger | |
| 4,256,050 | 3/1981 | Barnard | |
| 4,462,145 | 7/1984 | Schulze | |
| 4,817,318 | 4/1989 | Strauch | |
| 4,848,263 | 7/1989 | Grimm | 116/63 P X |

FOREIGN PATENT DOCUMENTS

| | | | |
|---|---|---|---|
| 1188988 | 3/1965 | Fed. Rep. of Germany | 116/63 P |
| 1395169 | 5/1975 | United Kingdom | |

*Primary Examiner*—Daniel M. Yasich
*Attorney, Agent, or Firm*—Boyd D. Cox

[57] ABSTRACT

A folding warning marker includes three tubular stays each having first upper ends joined together by torsional coil springs. A flexible, brightly colored and reflective fabric cover is received over the stays. The torsional coil springs bias each adjacent pair of the three stays apart, forming isosceles triangles such that the fabric cover forms a pyramidal configuration. An apex region of the flexible cover is reinforced to withstand the stress induced by the torsional coil springs. Lower ends of each of the tubular stays are received in respective pockets formed on an interior surface adjacent the lower peripheral edge of the fabric cover. The stays may be manually forced into a parallel relation to form a compact closed position of the warning marker for storage and transportation purposes. The warning marker may be retained in the closed position by a securing strap or a storage tube.

17 Claims, 2 Drawing Sheets

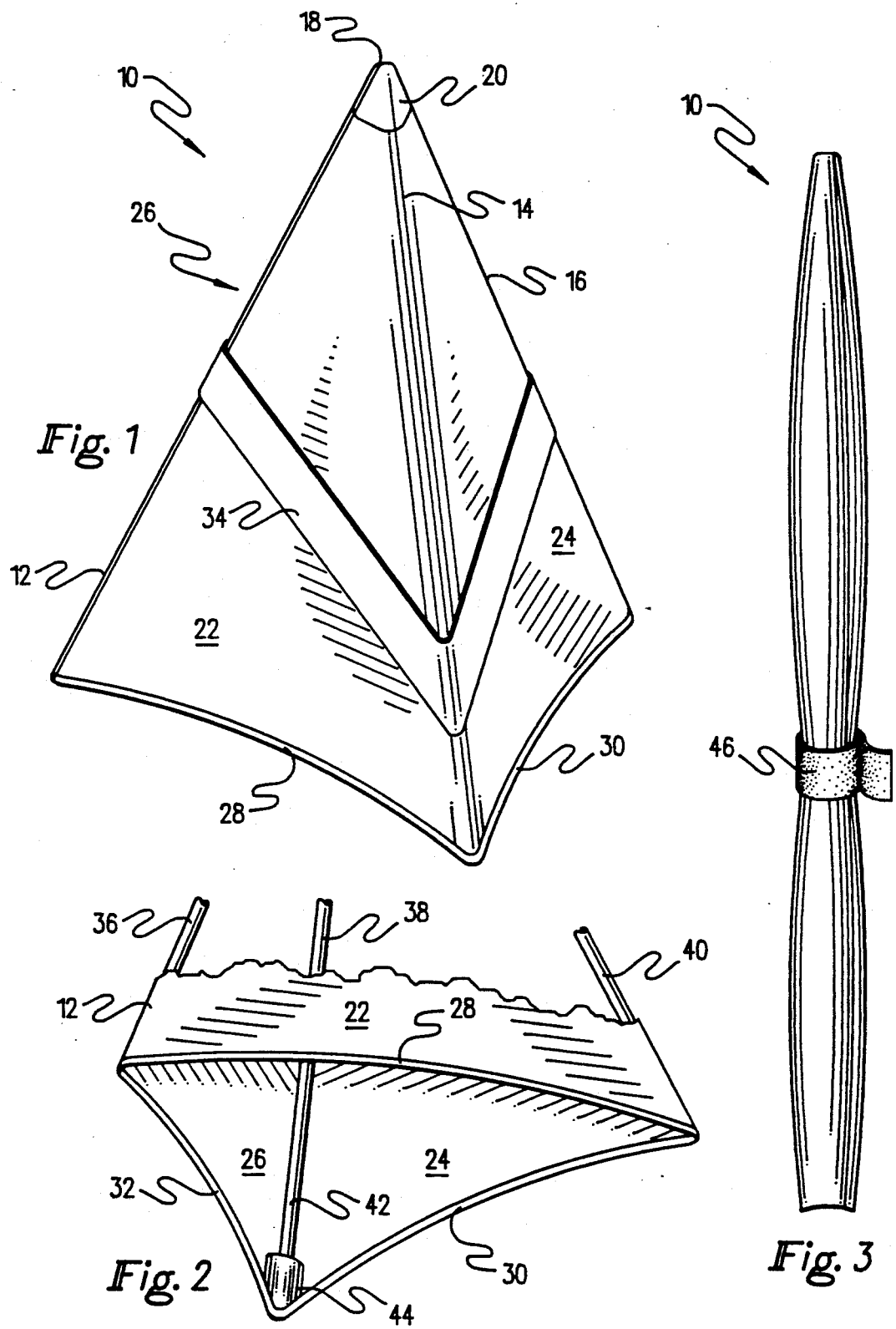

FOLDING WARNING MARKER

BACKGROUND OF THE INVENTION

FIELD OF THE INVENTION

The present invention relates to warning markers, and more particularly pertains to a warning marker of the type utilized as emergency highway and traffic markers or of the type utilized to warn individuals of other dangerous situations such as obstacles, wet or freshly waxed floors, etc. Such warning marker must be of a sufficient size so as to be readily visible, Yet must be small enough to be easily transportable and ready for emergency use. In order to achieve both of these objectives, the present invention is directed to a folding warning marker which is easily and automatically movable to an open position.

SUMMARY OF THE INVENTION

As such, the general purpose of the present invention, which will be described subsequently in greater detail, is to provide a new and improved folding warning marker which is easily transportable, inexpensive, and which automatically opens for use.

To attain this, a representative embodiment of the concepts of the present invention is illustrated in the drawings and makes use of a folding warning marker which includes three tubular stays each having first upper ends joined together by torsional coil springs. A flexible, brightly colored and reflective fabric cover is received over the stays. The torsional coil springs bias each adjacent pair of the three stays apart, forming isosceles triangles such that the fabric cover forms a pyramidal configuration. An apex region of the flexible cover is reinforced to withstand the stress induced by the torsional coil springs. Lower ends of each of the tubular stays are received in respective pockets formed on an interior surface adjacent the lower peripheral edge of the fabric cover. The stays may be manually forced into a parallel relation to form a compact closed position of the warning marker for storage and transportation purposes. The warning marker may be retained in the closed position by a securing strap or a storage tube.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the public generally, and especially those who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is another object of the present invention to provide a new and improved folding warning marker which may be easily and efficiently manufactured and marketed.

It is a further object of the present invention to provide a new and improved folding warning marker which is of a durable and reliable construction.

An even further object of the present invention is to provide a new and improved folding warning marker which is susceptible of a low cost of manufacture with regard to both materials and labor, and which accordingly is then susceptible of low prices of sale to the consuming public, thereby making such warning markers economically available to the buying public.

Still another object of the present invention is to provide a new and improved folding warning marker which is automatically movable between closed and open positions.

Yet another object of the present invention is to provide a new and improved folding warning marker which is movable to an extremely compact closed position for storage and transportation.

Even still another object of the present invention is to provide a new and improved folding warning marker which is movable to a compact closed position for storage and transportation in a relatively small storage tube.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of the folding warning marker of the present invention in an open pyramidal configuration.

FIG. 2 is a partial perspective detail view illustrating the manner of securing the lower ends of the supporting stays to the flexible cover of the folding warning marker.

FIG. 3 illustrates the folding warning marker in a closed position and secured by a strap.

DESCRIPTION OF THE PREFERRED EMBODIMENT

Figure 4:
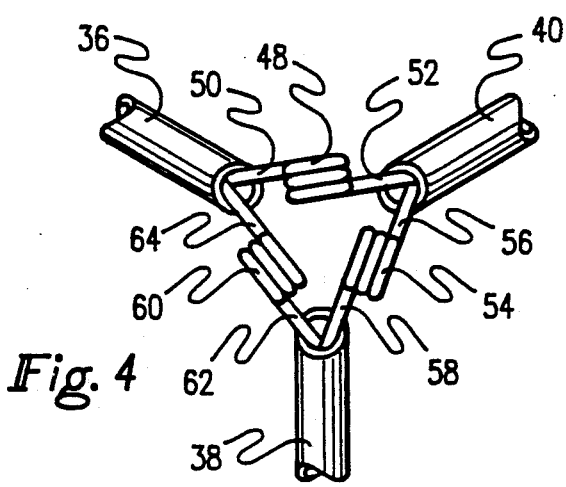
FIG. 4 is a partial, constructional detail perspective view illustrating the torsional coil spring mechanism for securing upper ends of the support stays and for biasing the support stays to an open position.

With reference now to the drawings, and in particular to FIG. 1 thereof, a new and improved folding warning marker embodying the principles and concepts of the present invention and generally designated by the reference numeral 10 will be described.

More specifically, it will be noted that the first embodiment 10 of the invention includes three corners 12, 14 and 16 and an upper apex 18. The pyramidal open configuration of the folding warning marker 10 shown in FIG. 1 is formed by a flexible cover having three triangular faces 22, 24 and 26. The upper apex zone 20 of the cover is reinforced, for example by utilizing a double fabric layer. A portion of the flexible cover may be reflective, as for example a reflective stripe or tape 34 may extend around the perimeter of the marker 10.

As can be appreciated from FIG. 2, the pyramidal configuration of the marker 10 is maintained by a plurality of tubular support stays 36, 38 and 40. The support stays 36, 38 and 40 each have a second lower end. The second lower end of each of the support stays 36, 38 and 40 is received in a corresponding pocket formed within the interior of the flexible cover. For example, the lower end 42 of stays 38 is received in a pocket 44 formed within the interior of the flexible cover. Thus, each of the support stays extends from a respective lower peripheral edge portion 28, 30 and 32 to the upper apex 18.

As shown in FIG. 3, the support stays 36, 38 and 40 may be manually urged to a generally parallel relationship, such that the marker 10 may be secured in a compact closed position by a securing strap 46. The strap 46 may be secured by cooperating hook and loop type fasteners, for example those sold under the trademark VELCRO. It should be noted that the marker 10 can be stored in this configuration by such means as a hook affixed to its upper end, said hook to be inserted through an eyelet mounted in a desired location. When the marker 10 is stored in this manner in a visible location and it is desired to maintain a certain color scheme at such location, stripes of a color in keeping with such color scheme may be aligned along the corners 12, 14 and 16. Thus, when the marker 10 is stored in a folded, closed position, substantially the only visible part of the marker 10 will be the stripes which can maintain the color scheme, while the remainder of the flexible cover can be of a more visible noticable color or material which will only be in evidence when the marker 10 is unfolded for use.

Figure 5:
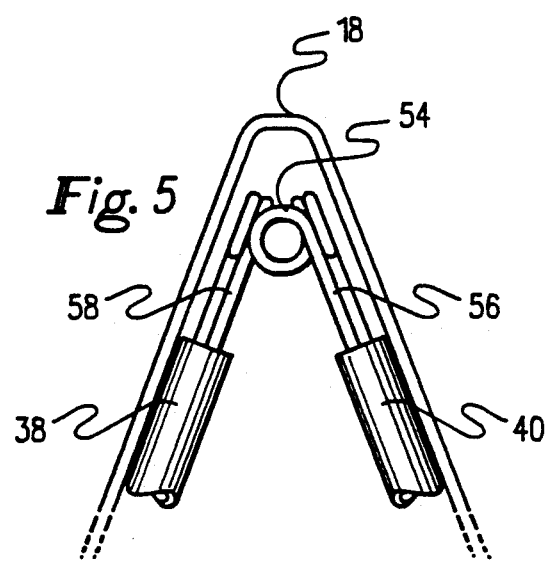
FIG. 5 is a partial side elevational view, further illustrating the torsional coil spring mechanism of FIG. 4.

FIGS. 4 and 5 illustrate a plurality of torsional coil springs 48, 54 and 60 which secure first or upper ends of the stays 36, 38 and 40 together in the region of the apex 18. Each of the torsional coil springs has first and second free ends which are received in respective support stays. For example, the spring 48 has first and second free ends 50 and 52 received in respective ones 36 and 40 of the support stays. Thus, spring 54 has respective first and second free ends 56 and 58 inserted within stays 40 and 38. Similarly, torsional coil spring 60 has free ends 62 and 64 inserted within respective tubular stays 38 and 36. As can now be understood, each of the torsional coil springs has first and second free ends inserted within a pair of adjacent support stays. This neutral securement is effective to bias the support stays 36, 38 and 40, outwardly away from the remaining pair of stays. The extent of outward movement of the support stays is limited by means retaining said stays within said cover such that the warning marker is movable between closed and open positions, comprising in the illustrated example embodiment, the configuration of the flexible cover and the securement of the lower ends of the support stays to the lower peripheral edge portion of the cover, as shown in FIG. 2. As can now be understood, this torsional coil spring mechanism, in conjunction with the shape of the cover, results in the formation of a three sided pyramidal configuration shown in FIG. 1. The lower or second ends of the support stays 36, 38 and rest upon a supporting surface in an open configuration, somewhat in the manner of a tripod.

Figure 6:
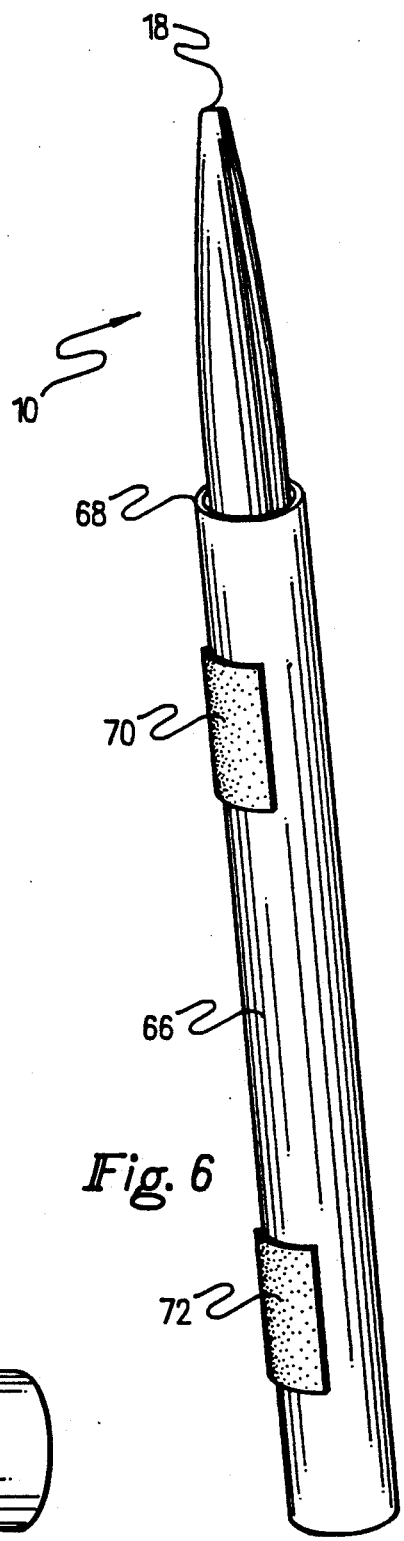
FIG. 6 is a perspective view illustrating the folding warning marker partially received within a storage tube.

As shown in FIG. 6, the following warning marker 10 may be inserted within the hollow interior of a storage tube 66 through an open end 68. The limited diameter of the tube 66 constrains the folding warning marker 10 to a compact position for purposes of storage and transportation. A plurality of hook and loop type fasteners 70 and 72 may be secured to the storage tube 66 for the purpose of fastening the storage tube 66 to an intended mounting surface.

Figure 7:
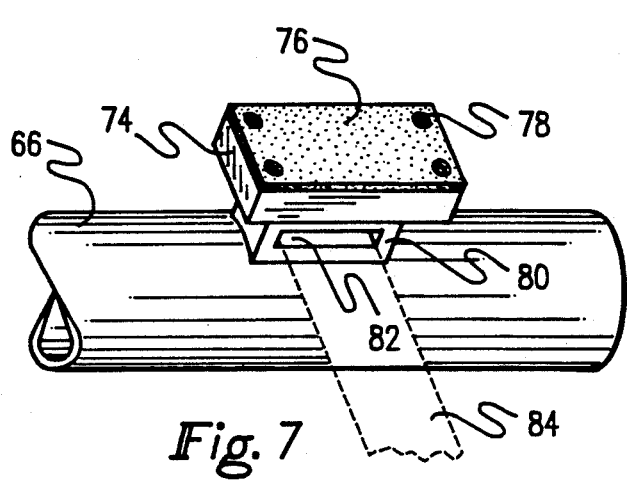
FIG. 7 is a partial perspective view illustrating an alternative storage tube for the folding warning marker including a mounting block for securing the storage tube to an intended mounting surface.

FIG. 7 illustrates an alternative mechanism for mounting the storage tube 66 comprising a mounting block 74 which may include an adhesive surface 76 and a plurality of aperture 78 adapted to receive mounting screws. A reduced neck position 80 of the mounting block 74 and includes a slot 82 for the reception of a mounting strap 84. The mounting strap 84 may include conventional fasteners, for example cooperating hook and loop type fasteners or buckles to assist in securing the storage tube 66 to the mounting block 74 and 80. In order to remove the storage tube 66, the mounting strap 84 is released and the tube 66 may then be moved away from the mounting block 74, 80. It should be understood that a plurality of the mounting blocks 74 may be positioned along the length of the tube 66.

It is contemplated that the flexible cover of the folding warning marker of the present invention may be formed from a bright warning color and from a durable fabric material such as nylon. The support stays are preferably formed from aluminum tubes, but may also be formed from non-metallic materials such as fiberglass. In this connection, it should be understood that the torsional coil springs may be embedded or inserted into holes drilled into the ends of the stays or otherwise connected to the stays if non-tubular stays are employed. It should further be understood that while the invention has been described and illustrated with respect to cylindrical stays, flat, square, hexagonal or various other shaped stays may be employed, without departing from the scope and content of the present invention. Additionally, while the invention has been described with reference to the use of three stays, two or a number greater than three stays may also be employed.

With reference to the foregoing, the manner of use and advantages of the folding warning marker according to the present invention may now be readily understood. The marker may be easily stored in a minimum amount of space in locations where most frequently needed, for example on cars, carts, near high traffic areas, etc. Additionally, the marker has a pyramidal configuration and thus can be seen from all directions. The marker is extremely inexpensive and thus more economically available to facilitate wider use. The flexible cover can be imprinted with various messages, for example "CAUTION", "WET FLOOR", "DANGER", "CLOSED", "DO NOT ENTER", etc. Further, changeable messages may be secured to the outer surface of the flexible cover by means of cooperating hook and loop type fasteners or tacky adhesives.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A folding warning marker, comprising:
    a plurality of elongated tubular stays;
    means securing first ends of said stays and urging said stays apart comprising at least one torsional coil spring having opposite free ends received in respective said first ends of said stays;
    a flexible cover over said stays; and
    means retaining said stays within said cover such that said warning marker is movable between closed and open positions.

2. The folding warning marker of claim 1, wherein said folding warning marker includes at least three stays.

3. The folding warning marker of claim 1, wherein said means retaining said stays within said cover comprises a plurality of pockets on said cover receiving second ends of said stays.

4. The folding warning marker of claim 1, wherein said cover includes a reinforced zone adjacent said first ends of said stays.

5. The folding warning marker of claim 1, wherein said folding warning marker possesses a pyramidal shape in said open position.

6. The folding warning marker of claim 1, further comprising a storage tube for transporting and storing said folding warning marker in said closed position.

7. The folding warning marker of claim 6, further comprising means for securing said storage tube to an intended mounting surface for facilitate transportation and storage of said folding warning marker.

8. The folding warning marker of claim 7, wherein said means for securing said storage tube comprises cooperating hook and loop fastening members.

9. The folding warning marker of claim 1, wherein said cover includes at least one reflective portion.

10. The folding warning marker of claim 1, further comprising a securing strap for retaining said folding warning marker in said closed position.

11. A folding warning marker, comprising:
    a plurality of elongated stays;
    means securing first ends of said stays and urging said stays part;
    a flexible cover over said stays;
    means retaining said stays within said cover such that said warning marker is movable between closed and open positions; and
    a storage tube for transporting and storing said folding warning marker in said closed position; and
    means for securing said storage tube to an intended mounting surface to facilitate transportation and storage of said folding warning marker including at least one mounting block on said tube possessing a slot for receiving a mounting strap.

12. A folding warning marker movable between closed and open positions, comprising:
    three elongated says, each having first and second opposite ends;
    three torsional coil springs, each having first and second opposite free ends;
    each of said torsional coil springs having said first and second free ends secured respectively to said first ends of two adjacent ones of said three stays and biasing said stays apart, to said open position;
    a flexible cover over said stays;
    said second ends of said stays secured adjacent a lower end of said cover; and
    said cover dimensioned to form a pyramidal configuration in said open position such that each adjacent pair of said stays forms the sides of a triangle.

13. The folding warning marker of claim 12, wherein each of said second ends of said stays is received in a corresponding pocket formed on an interior surface of said cover.

14. The folding warning marker of claim 12, wherein each of said stays comprises a tube and said first and second ends of said torsional coil springs are received in said tubes.

15. The folding warning marker of claim 12, further comprising a storage tube for transporting and storing said folding warning marker in said closed position.

16. The folding warning marker of claim 15, further comprising means for securing said storage tube to an intended mounting surface for facilitating transportation and storage of said folding warning marker.

17. A folding warning marker, comprising:
    a plurality of elongated stays;
    means securing first ends of said stays and urging said stays apart comprising at least one torsional coil spring having opposite free ends received in respective said first ends of said stays;
    a flexible cover over said stays; and
    means retaining said stays within said cover such that said warning marker is movable between closed and open positions.

* * * * *

UNITED STATES PATENT AND TRADEMARK OFFICE
CERTIFICATE OF CORRECTION

PATENT NO. : 5,199,375
DATED : April 6, 1993
INVENTOR(S) : Mike V. Johnson

It is certified that error appears in the above-identified patent and that said Letters Patent is hereby corrected as shown below:

Column 4, line 23, insert the number --40-- after the word "and".

In Claim 7, Column 6, line 1 of the Patent, change "for" to --to--.

In Claim 12, Column 6, line 28 of the Patent, change "says" to --stays--.

Signed and Sealed this

Thirtieth Day of November, 1993

Attest:

BRUCE LEHMAN

*Attesting Officer*  *Commissioner of Patents and Trademarks*